(12) United States Patent
Babaev

(10) Patent No.: US 6,601,581 B1
(45) Date of Patent: Aug. 5, 2003

(54) METHOD AND DEVICE FOR ULTRASOUND DRUG DELIVERY

(75) Inventor: Eilaz Babaev, Minnetonka, MN (US)

(73) Assignee: Advanced Medical Applications, Inc., Eden Prairie, MN (US)

( * ) Notice: Subject to any disclaimer, the term of this patent is extended or adjusted under 35 U.S.C. 154(b) by 88 days.

(21) Appl. No.: 09/704,099

(22) Filed: Nov. 1, 2000

(51) Int. Cl.$^7$ .............................................. B05B 17/06
(52) U.S. Cl. ............................ 128/200.16; 239/102.2; 604/58
(58) Field of Search ...................... 128/200.14, 200.16, 128/203.12, 203.15; 604/48, 514, 57, 58; 239/102.2

(56) References Cited

U.S. PATENT DOCUMENTS

| | | | |
|---|---|---|---|
| 3,275,059 A | 9/1966 | McCullough | 431/74 |
| 3,392,916 A | 7/1968 | Engstrom et al. | 239/102.2 |
| 3,561,444 A * | 2/1971 | Boucher | 128/200.16 |
| 3,860,173 A | 1/1975 | Sata | 239/102.2 |
| 4,052,004 A | 10/1977 | Martin et al. | 239/102.2 |
| 4,085,893 A | 4/1978 | Durley, III | 239/102.2 |
| 4,153,201 A | 5/1979 | Berger et al. | 239/102.2 |
| 4,251,031 A | 2/1981 | Martin et al. | 239/102.2 |
| 4,271,705 A * | 6/1981 | Crostack | 367/137 |
| 4,294,407 A | 10/1981 | Reichl et al. | 239/102.2 |
| 4,301,093 A * | 11/1981 | Eck | 128/200.16 |
| 4,301,968 A | 11/1981 | Berger et al. | 239/102.2 |
| 4,309,989 A | 1/1982 | Fahim | 128/24 A |
| 4,319,155 A * | 3/1982 | Nakai et al. | 128/200.16 |
| 4,334,531 A * | 6/1982 | Reichl et al. | 128/200.14 |
| 4,352,459 A | 10/1982 | Berger et al. | 239/102.2 |
| 4,428,531 A | 1/1984 | Martin | 239/569 |
| 4,466,571 A | 8/1984 | Muhlbauer | 239/101 |
| 4,530,360 A | 7/1985 | Duarte | 607/51 |
| 4,541,564 A | 9/1985 | Berger et al. | 239/102.2 |
| 4,582,654 A * | 4/1986 | Karnicky et al. | 239/102.2 |
| 4,619,400 A | 10/1986 | van der Burgt | 239/102.1 |
| 4,642,581 A | 2/1987 | Erickson | 331/154 |
| 4,655,393 A | 4/1987 | Berger | 239/102.1 |
| 4,659,014 A | 4/1987 | Soth et al. | 239/102.2 |
| 4,679,551 A | 7/1987 | Anthony | 601/160 |
| 4,726,523 A | 2/1988 | Kokubo et al. | 239/102.2 |

(List continued on next page.)

FOREIGN PATENT DOCUMENTS

| | | | | |
|---|---|---|---|---|
| EP | 0 156 4009 A2 | 2/1985 | | |
| EP | 0 437 155 B1 | 2/1990 | | |
| EP | 0 657 226 B1 | 11/1994 | | |
| GB | 2099710 A * | 12/1982 | | A61M/11/00 |
| GB | 2 099 710 A | 12/1982 | | |
| GB | 2 101 500 A | 1/1983 | | |
| GB | 2101500 A * | 1/1983 | | B05B/17/06 |
| JP | 2000237275 A2 | 9/2000 | | |
| WO | WO 96/35383 | 11/1996 | | |

OTHER PUBLICATIONS

Journal of Burn Care & Rehabilitation; vol. 21, No. 4; Jul./Aug. 2000 pp. 333–338.

Design and Application of Low–Frequency Ultrasound and Its Combination With Laser Radiation in Surgery and Therapy—Critical Reviews in Biomedical Engineering; 2001; pp. 502–519.

Primary Examiner—Edward K. Look
Assistant Examiner—Richard A. Edgar
(74) Attorney, Agent, or Firm—Carter, DeLuca, Farrell & Schmidt, LLP

(57) ABSTRACT

The present invention concerns a device for creating a directed spray of liquid or powder particles which is produced by contacting the liquid of powder with a radiation surface of an ultrasonic transducer such as a piezofilm or ultrasound tip. The ultrasonic waves cause the spray to project outwardly from the radiation surface and directs it into a patient's mouth or onto another target. Directed particle spray delivers sharp dosage and uniformed up to 90% particle size drug delivery.

26 Claims, 3 Drawing Sheets

U.S. PATENT DOCUMENTS

| | | | |
|---|---|---|---|
| 4,726,525 A | 2/1988 | Yonekawa et al. | 239/102.2 |
| 4,733,820 A | 3/1988 | Endo et al. | 239/102.2 |
| 4,756,478 A | 7/1988 | Endo et al. | 239/102.2 |
| 4,783,003 A | 11/1988 | Hirabayashi et al. | 239/102.2 |
| 4,790,479 A | 12/1988 | Matsumoto et al. | 239/102.2 |
| 4,793,339 A * | 12/1988 | Matsumoto et al. | 128/200.16 |
| 4,850,534 A | 7/1989 | Takahashi et al. | 239/102.2 |
| 4,877,989 A * | 10/1989 | Drews et al. | 128/200.16 |
| 4,905,671 A | 3/1990 | Senge et al. | 601/4 |
| 4,930,700 A | 6/1990 | McKown | 239/102.2 |
| 4,941,618 A | 7/1990 | Hildebrand et al. | 239/432 |
| 4,961,885 A | 10/1990 | Avrahami et al. | 261/142 |
| 5,002,059 A | 3/1991 | Crowley et al. | 600/466 |
| 5,040,537 A | 8/1991 | Katakura | 600/431 |
| 5,063,922 A | 11/1991 | Hakkinen | 128/200.16 |
| 5,076,266 A | 12/1991 | Babaev | 128/200.16 |
| 5,104,042 A | 4/1992 | McKown | 239/102.2 |
| 5,115,805 A | 5/1992 | Bommannan et al. | 601/2 |
| 5,134,993 A * | 8/1992 | van der Linden et al. | 128/200.14 |
| 5,163,433 A | 11/1992 | Kagawa et al. | 601/2 |
| 5,172,692 A | 12/1992 | Kulow et al. | 601/2 |
| 5,186,162 A | 2/1993 | Talish et al. | 601/2 |
| 5,197,946 A | 3/1993 | Tachibana | 604/22 |
| 5,211,160 A | 5/1993 | Talish et al. | 601/2 |
| 5,231,975 A | 8/1993 | Bommannan et al. | 601/2 |
| 5,269,291 A | 12/1993 | Carter | 606/128 |
| 5,315,998 A | 5/1994 | Tachibana et al. | 601/2 |
| 5,316,000 A | 5/1994 | Chapelon et al. | 600/439 |
| 5,318,014 A | 6/1994 | Carter | 606/128 |
| 5,323,769 A | 6/1994 | Bommannan et al. | 601/2 |
| 5,324,255 A | 6/1994 | Passafaro et al. | 604/22 |
| 5,345,940 A | 9/1994 | Seward et al. | 600/463 |
| 5,347,998 A | 9/1994 | Hodson et al. | 128/200.23 |
| 5,362,309 A | 11/1994 | Carter | 604/22 |
| 5,374,266 A | 12/1994 | Kataoka et al. | 606/15 |
| 5,380,411 A | 1/1995 | Schlief | 204/157.15 |
| 5,393,296 A | 2/1995 | Rattner | 601/2 |
| 5,437,606 A | 8/1995 | Tsukamoto | 601/2 |
| 5,515,841 A * | 5/1996 | Robertson et al. | 128/200.14 |
| 5,515,842 A * | 5/1996 | Ramseyer et al. | 128/200.14 |
| 5,516,043 A | 5/1996 | Manna et al. | 239/102.2 |
| 5,520,166 A | 5/1996 | Ritson et al. | 128/200.14 |
| 5,520,612 A | 5/1996 | Winder et al. | 601/2 |
| 5,527,350 A | 6/1996 | Grove et al. | 607/89 |
| 5,529,572 A | 6/1996 | Spector | 601/2 |
| 5,545,124 A | 8/1996 | Krause et al. | 601/2 |
| 5,551,416 A | 9/1996 | Stimpson et al. | 128/200.16 |
| 5,554,172 A | 9/1996 | Horner et al. | 607/88 |
| 5,556,372 A | 9/1996 | Talish et al. | 601/2 |
| 5,573,497 A | 11/1996 | Chapelon | 601/2 |
| 5,616,140 A | 4/1997 | Prescott | 606/10 |
| 5,626,554 A | 5/1997 | Ryaby et al. | 601/2 |
| 5,643,179 A | 7/1997 | Fujimoto | 601/2 |
| 5,656,016 A | 8/1997 | Ogden | 601/2 |
| 5,658,323 A | 8/1997 | Miller | 607/89 |
| 5,699,805 A | 12/1997 | Seward et al. | 600/459 |
| 5,707,402 A | 1/1998 | Heim | 607/88 |
| 5,707,403 A | 1/1998 | Grove et al. | 607/89 |
| 5,730,705 A | 3/1998 | Talish et al. | 601/2 |
| 5,735,811 A | 4/1998 | Brisken | 604/22 |
| 5,743,863 A | 4/1998 | Chapelon | 601/2 |
| 5,752,924 A | 5/1998 | Kaufman et al. | 601/2 |
| 5,762,616 A | 6/1998 | Talish | 601/2 |
| 5,785,972 A | 7/1998 | Tyler | |
| 5,835,678 A | 11/1998 | Li et al. | 392/401 |
| 5,843,139 A | 12/1998 | Goedeke et al. | 607/32 |
| 5,879,314 A | 3/1999 | Peterson et al. | 601/2 |
| 5,879,364 A | 3/1999 | Bromfield et al. | 606/169 |
| 5,882,302 A | 3/1999 | Driscoll, Jr. et al. | 600/371 |
| 5,894,841 A | 4/1999 | Voges | 128/203.12 |
| 5,947,921 A | 9/1999 | Johnson et al. | 604/22 |
| 5,960,792 A | 10/1999 | Lloyd et al. | 128/203.22 |
| 5,989,245 A | 11/1999 | Prescott | 606/14 |
| 6,001,069 A | 12/1999 | Tachibana et al. | 601/2 |
| 6,014,970 A | 1/2000 | Ivri et al. | 128/200.16 |
| 6,024,718 A | 2/2000 | Chen et al. | 604/22 |
| 6,026,808 A | 2/2000 | Armer et al. | 128/200.23 |
| 6,027,495 A | 2/2000 | Miller | 606/9 |
| 6,041,253 A | 3/2000 | Kost et al. | 604/22 |
| 6,061,597 A | 5/2000 | Rieman et al. | 607/51 |
| 6,076,519 A | 6/2000 | Johnson | 128/200.14 |
| 6,083,159 A | 7/2000 | Driscoll, Jr. et al. | 600/371 |
| 6,095,141 A | 8/2000 | Armer et al. | 128/204.26 |
| 6,098,620 A | 8/2000 | Lloyd et al. | 128/204.23 |
| 6,102,298 A | 8/2000 | Bush et al. | 239/4 |
| 6,104,952 A | 8/2000 | Tu et al. | |
| 6,106,547 A | 8/2000 | Huei-Jung | 607/96 |
| 6,113,558 A | 9/2000 | Rosenschein et al. | 601/2 |
| 6,113,570 A | 9/2000 | Siegel et al. | 604/507 |
| RE36,939 E | 10/2000 | Tachibana et al. | |
| 6,176,839 B1 | 1/2001 | Deluis et al. | 601/2 |
| 6,186,963 B1 | 2/2001 | Schwarze et al. | 601/2 |
| 6,190,315 B1 | 2/2001 | Kost et al. | 600/309 |
| 6,190,336 B1 | 2/2001 | Duarte et al. | 601/2 |
| 6,206,842 B1 | 3/2001 | Tu et al. | 601/2 |
| 6,206,843 B1 | 3/2001 | Iger et al. | 601/2 |
| 6,231,528 B1 | 5/2001 | Kaufman et al. | 601/2 |
| 6,234,990 B1 | 5/2001 | Rowe et al. | 604/22 |
| 6,251,099 B1 | 6/2001 | Kollias et al. | |
| 6,273,864 B1 | 8/2001 | Duarte et al. | 601/2 |
| 6,296,630 B1 | 10/2001 | Altman et al. | |
| 6,321,109 B2 | 11/2001 | Ben-Haim et al. | 600/424 |
| 6,322,527 B1 | 11/2001 | Talish | 601/2 |
| 6,325,769 B1 | 12/2001 | Klopotek | 601/2 |

\* cited by examiner

METHOD AND DEVICE FOR ULTRASOUND DRUG DELIVERY

FIELD OF THE INVENTION

The present invention relates to a drug delivery system. In particular the present invention relates to a pocket size or hand held ultrasonic-pulmonary drug delivery system.

BACKGROUND OF THE INVENTION

In many medical applications it is necessary to make aerosols from liquids and powders. One of the therapeutic medical uses of ultrasound waves is in liquid aerosol mist production. Aerosol mist production makes use of a nebulizer or inhaler to produce an aerosol mist for creating a humid environment and delivering a drug to the lung.

Particularly for oral-pulmonary applications it is necessary to atomize medications, such as antibiotics, insulin, asthma drugs, and other drugs to make an aerosol that reaches the mouth, boucle, intestine and consequently the lungs.

Ultrasonic nebulizers operate by passing ultrasound waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred because a smaller particle size of the aerosol can be obtained with the ultrasonic waves.

One of the major shortcomings of known ultrasonic inhalers and nebulizers is that there is no directed aerosol to the target. Therefore, an air stream is required to direct the aerosol to the target; however, this decreases the efficiency of ultrasound mist.

The device of the present invention comprises a means for creating a directed spray of liquid or powder particles produced by contact of the liquid or powder with a radiation surface of any ultrasound transducer such as, for example, a piezofilm or ultrasound tip. The ultrasonic waves cause the spray to project outwardly from the radiation surface of the transducer, and a particle spray is directed to the mouth.

Accordingly, the device of the present invention generates a directed particle spray, created by ultrasound waves, into a mouth and delivers a sharp dosage of a uniform up to 90% particle size drug.

Furthermore, the ultrasound waves used in the device energize the drug and cause penetration of the drug below the surface of the tissue.

Finally, the device of the present invention for drug delivery is particularly advantageous when sharp dosage drug delivery is desirable, such as, for example, with insulin for diabetic care. Piezoelectric oscillatory and liquid atomization system, is known with a bending oscillator or working plate for atomization of liquid. A disadvantage of these piezoelectric atomizers is that the particle sizes are not uniform and particle sizes of about 0.1 micron to several millimeters are obtained. The particles of larger diameter must be retained by means of a mechanical droplet separator.

A number of prior art references are available in the art, each of which references are directed to some specific discreet elements of the system which is described and claimed in the present invention, however, none of which is directed to the totality of the combination, or its use and function in the manner described and claimed herein:

Ultrasonic sprayers from Sonic and Materials, Inc., Misonix, Inc., Sono-Tek, Inc., Zevex International, Inc. U.S. Pat. Nos. 3,765,606, 4,659,014, 5,104,042, 4,930,700, 4,153,201, 4,655,393, 5,516,043, 5,835,678, 5,879,364 and 5,843,139, etc., operate by passing liquid through a central orifice of an ultrasound instrument tip which creates problems with dosage control, heating of the drug, non-uniform particles, and other related difficulties.

Ultrasonic inhalers and drug delivery systems from Medisonic USA, Inc., 3M, Siemens Gmb, The Procter Gamble Company, Sheffield Pharmaceuticals, Aradigm, Inc., U.S. Pat. Nos. 4,294,407, 5,347,998, 5,520,166, 5,960,792, 6,095,141, 6,102,298, 6,098,620, 6,026,808, and 6,106,547, operate by atomizing liquid using piezoceramic film and air/propellant.

U.S. Pat. No. 4,912,357 describes a MHz oscillator with a concave surface adapted to the defined (limited $V \leq$) liquid quantity to be atomized.

In U.S. Pat. No. 5,950,619 a propellant is used along with ultrasound. Another disadvantage of this device is that the atomization surface is button shaped, which creates uniform particles, and the distance between valve and atomization surface is hardly achievable in industrial assemble process (0.1 to 0.5 mm).

U.S. Pat. Nos. 5,586,550, 5,758,637, 5,938,117, 6,014, 970, and 6,085,740 are based in driving liquid through the hole made on a piezofilm's working area. Bending waves are used, which spray non-uniform liquid particles.

U.S. Pat. No. 5,261,601 describes an atomizer having a membrane covering a liquid chamber. U.S. Pat. No. 4,533, 082 describes a liquid sprayer with multiple orifices on the vibrating element.

OBJECTS OF THE INVENTION

It is an object of the present invention to provide an improved device for oral pulmonary drug delivery.

It is also an object of the present invention to provide an improved device for oral pulmonary drug delivery using ultrasonic waves.

It is another object of the present invention to provide a device for the delivery of drugs ultrasonically with high efficiency.

It is yet another object of the present invention to provide a device for the delivery of drugs without the use of air or other propellants.

It is therefore an object of the present invention to provide a device for delivering drugs which affords highly precise dosage control.

It is a further object of the present invention to provide a method for the delivery of uniformed particles of a drug using ultrasonic waves.

These and other objects of the invention will become apparent from the following discussion below.

SUMMARY OF THE INVENTION

The present invention provides for a drug delivery system. More particularly the present invention provides for a pocket size or hand held ultrasonic oral—pulmonary liquid and powder drug delivery device.

In one embodiment the device of present invention is characterized in that it is able to produce a spray and deliver it to the oral/pulmonary tract, without use of air or other propellants and with such spray having greater than about 90% uniform particle size, with a high degree of dosage control.

The device of the invention comprises means for creating a directed spray of liquid or powder particles produced by contact of the liquid or powder with a radiation surface of ultrasound transducer such as, for example, a piezofilm/disk or ultrasound tip. The ultrasonic waves produced cause the spray to project outwardly from the radiation surface of the transducer. The particle spray is directed into the mouth for oral/pulmonary delivery.

According to the device of the present invention directed particle spray, created by ultrasound waves into a mouth delivers sharp dosage and uniform up to 90% particle size drug.

Furthermore, the ultrasonic waves used in the device, energize the drug and cause penetration of the drug below the surface of the tissue.

Finally, the device of the invention for drug delivery is particularly advantageous when sharp dosage drug delivery is desirable, such as in insulin therapy for diabetic care, and similar applications.

The construction and obvious advantages of the system provided for by the present invention will be more clearly understood from the following description of the various specific embodiments when read in conjunction with the accompanying drawings.

DETAILED DESCRIPTION OF THE INVENTION

The present invention is directed to a method and device for ultrasonic aerosol drug delivery, characterized by a means for first delivering a liquid or powder drug to a radiation surface of a piezofilm/disk or ultrasonic transducer tip such that the liquid is dropped to the radiation surface under gravity. For this purpose, and to easily produce a spray, the radiation surface of the piezofilm/disk or ultrasonic transducer must be placed at some angle with relation the horizontal. The actual radiation surface or geometric form of the ultrasound transducer tip may be one of many different shapes, such as, for example, cylindrical, oval, elliptical, square, rectangular, multi-angular, or another shape. Furthermore, the placement of the radiation surface at some angle allows one to get aerosol spray emanating from one point that is the touch point of the liquid with the radiation surface, which is a very important consideration and critical to obtaining uniform aerosol particle size. With the method and device of the present invention one is able to achieve substantial uniformity of particle size, to a degree of about 90% or greater.

The step of producing the aerosol spray preferentially includes operating the transducer in such a manner as to produce ultrasonic waves having a frequency of from about 18 kHz to about 10,000 MHz. It is within the scope of the invention that the frequency could be less than about 18 kHZ or greater than 10,000 MHz.

The frequency may be constant, modulated or pulsed. The wave form produced may be sinusoidal, rectangular, trapezoid or triangular.

Frequencies below 18 kHz can be used as well; however, lower frequencies are less desirable due the fact that this range of sonic, or sound, waves can be uncomfortable to the patient. A most preferred range of frequencies is from about 20 to 200 kHz. Frequencies of about 100 kHz are most preferred.

The device and method of the present invention can also include means for directing the spray into the mouth or at a target for from about 1 second to about 30 minutes, dependant upon the required dosage. The liquid or powder to be sprayed can include any drug, such as, for example, an antibiotic or antiseptic, and/or liquid which can be, for example, saline, water (distilled or regular), or oil.

The distance between the radiation surface of the transducer or piezofilm/disk and the liquid tube will. preferably be about the size of liquid drop diameter ≈0.5 mm and above. Distances of less than 0.5 mm (up to 50 micron) can be used as well; however, this may cause some assembly difficulties.

In one preferred embodiment the method and device of present invention provides aerosol drug delivery with no air stream, no propellant and no pressure.

Figure 1:
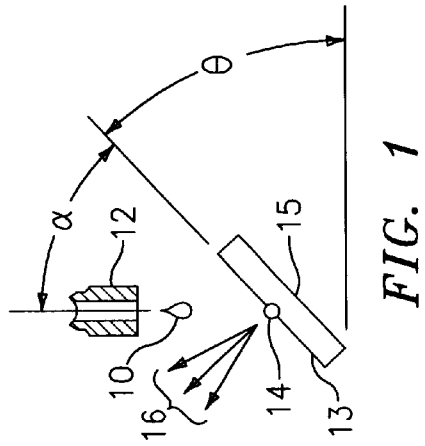
FIG. 1 is perspective view of the concept of an ultrasonic aerosol drug delivery device according to the present invention showing the principal elements as they relate to one another.

FIG. 1 depicts a basic concept of the ultrasonic aerosol drug delivery method and device according to the invention. A liquid (drug) drop or flow 10 falls under gravity to a radiation surface 13 of piezofilm/disk 15 via dispenser tube 12. Drop 10 contacts surface 13 at point 14 and creates directed aerosol 16. Radiation surface 13 of piezofilm/disk 15 is placed at an angle θ with respect to the horizontal.

Figure 2:
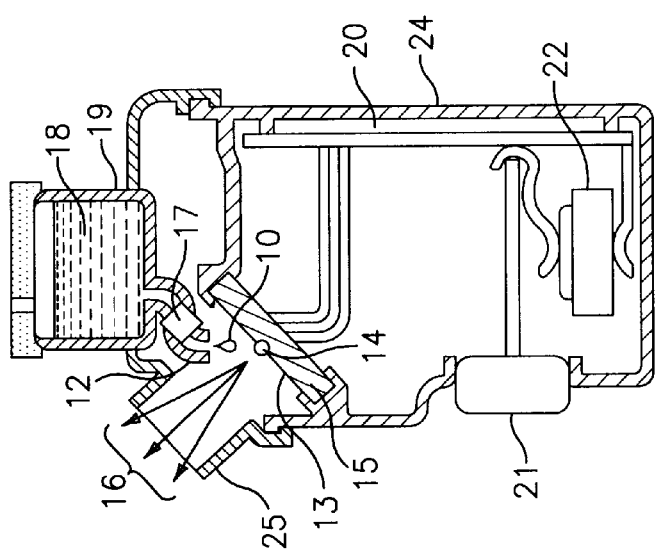
FIG. 2 is a lateral cross-sectional elevational view of one embodiment of the ultrasonic aerosol drug delivery device according to the invention with a piezofilm or piezodisc working element.

In FIG. 2, which depicts a cross-sectional view of one preferred embodiment of the aerosol drug delivery device according to the invention, housing 24 includes piezofilm/disk 15 and liquid reservoir 19, which is may or may not be disposable. Housing 24 is also provided with a liquid dispenser 17, an electronic circuit board 20, a battery or capacitor 22, and an on/off button 21. Button 21 activates electronic circuit board 20, which is electrically connected to piezofilm/disk and causes piezofilm/disk 15 to oscillate. Liquid 18 from reservoir 19 is dispensed and delivered to radiation surface 13 (with an amplitude of ultrasound waves greater than 5 microns) at contact point 14, creating aerosol 16 which is directed to a mouth/target (not shown). Nozzle 25, which directs aerosol 16 into a patient's mouth/target, may or may not be disposable.

Figure 3:
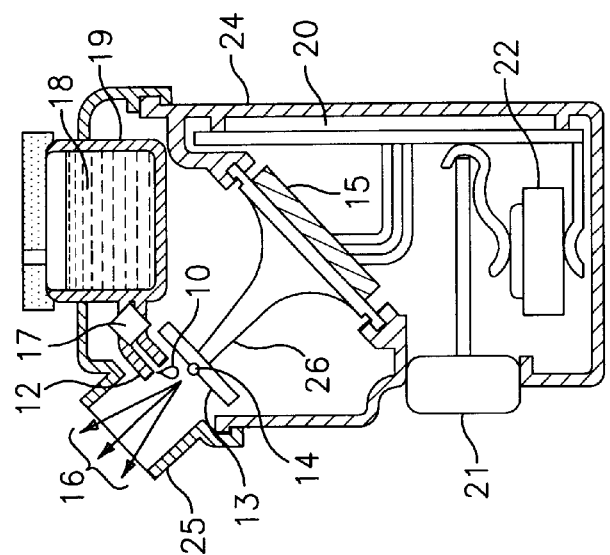
FIG. 3 is a lateral cross-sectional elevational view of another embodiment of the ultrasonic aerosol drug delivery device according to the invention, using an ultrasound tip with an enlarged distal end/radiation surface placed at an angle.

FIG. 3 depicts a cross-sectional view of another embodiment of the aerosol drug delivery device according to the invention having an ultrasound transducer tip. The convenient location of surface 13 of a transducer tip 26 at an angle with the horizontal allows liquid or powder drop 10 delivered to the contact point 14 with gravity. The distance between distal end of tube 12 and contact point 14 or radiation surface 13 is less than or equal to the diameter of the liquid drop, and the aerosol drug delivery device will work in any position. If this distance between the distal end of tube 12 and contact point 14 on surface 13 is greater then a drop's diameter, then the device will only work vertically, which should not create a problem for the user.

Figure 4:
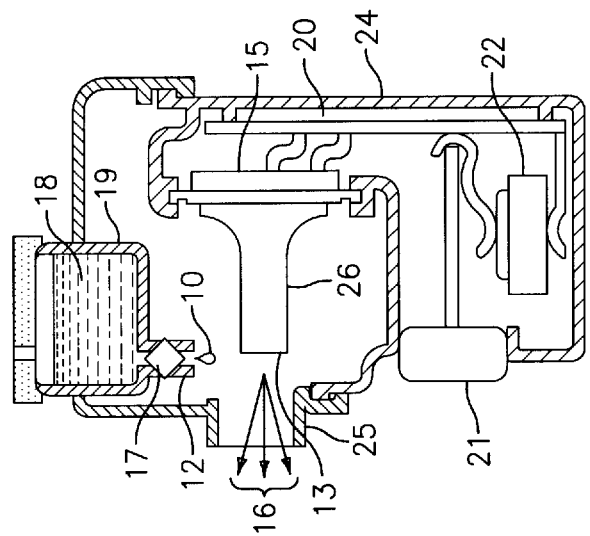
FIG. 4 is a lateral cross-sectional elevational view of another embodiment of the ultrasonic aerosol drug delivery device according to the invention, using an ultrasound tip with an enlarged distal end/radiation surface placed horizontally.

FIG. 4 is a cross-sectional view of another preferred embodiment of the ultrasonic aerosol drug delivery device according to the invention with a transducer tip 26. As illustrated, in this case liquid drop 10 must be directed exactly to the corner of the radiation surface of ultrasound tip 26. After touching the corner, liquid drop 10 pulls to the radiation surface 13, spreads and is aerosolized and directed to the mouth/target.

Figure 5:
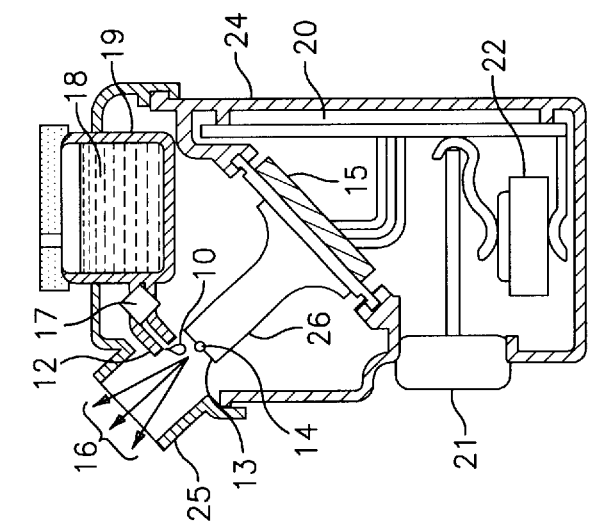
FIG. 5 is a lateral cross-sectional elevational view of another embodiment of the ultrasonic aerosol drug delivery device according to the invention, using an ultrasound tip with a cylindrical distal end/radiation surface placed at an angle.
Figure 6:
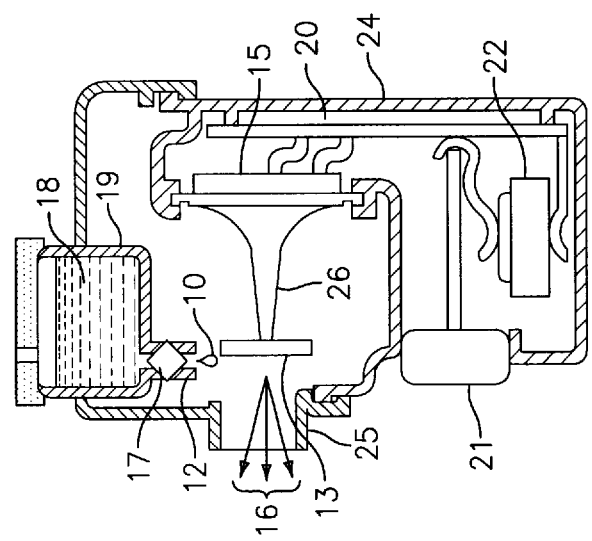
FIG. 6 is a lateral cross-sectional elevational view of another embodiment of ultrasonic aerosol drug delivery device according to the invention, using an ultrasound tip with the cylindrical end/radiation surface, placed horizontally.

With reference to FIGS. 5 and 6, which illustrate cross-sectional views of another preferred embodiment of the present invention, shown are a regular and cylindrical ultrasound transducer tip placed at an angle and horizontally, respectively.

Figure 7:
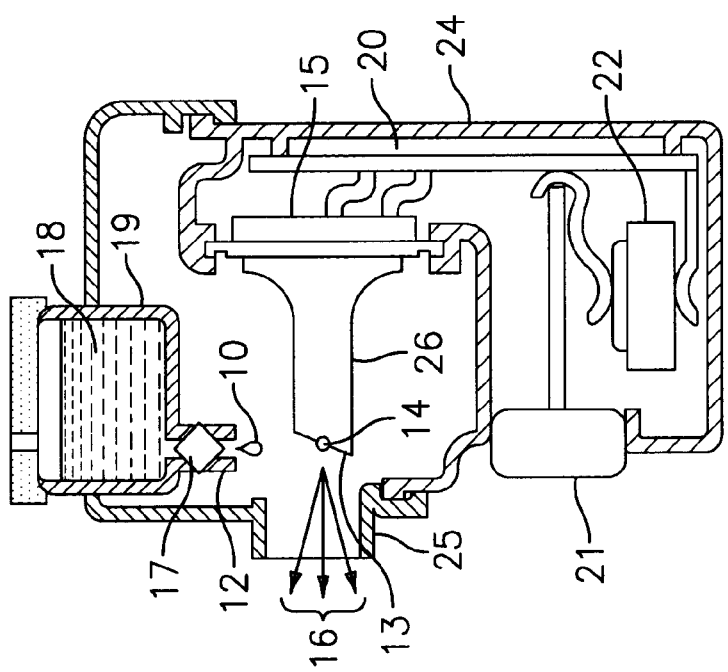
FIG. 7 is a lateral cross-sectional elevational view of another embodiment of the ultrasonic aerosol drug delivery device according to the invention, using an ultrasound tip with a truncated angled distal end/radiation surface, placed horizontally.

With reference to FIG. 7, which illustrates a cross-sectional view of another embodiment according to the invention, shown is truncated ultrasound tip 26, which allows one to create a liquid or powder aerosol spray more easily.

Figure 8:
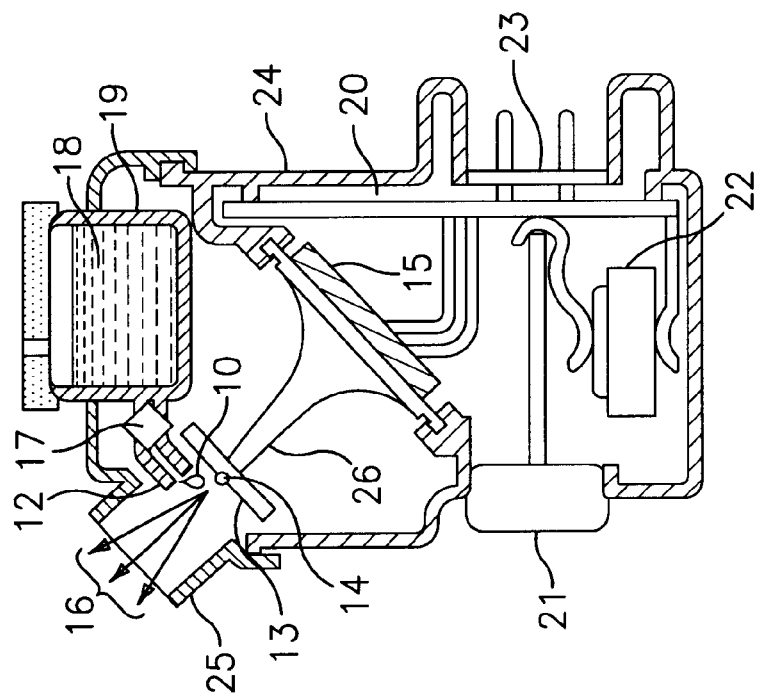
FIG. 8 is a lateral cross-sectional elevational view of another embodiment of the ultrasonic aerosol drug delivery device according to the invention, using an alternative power supply as an AC adaptor.

With reference to FIG. 8, which illustrates a cross-sectional view of another preferred embodiment according to the invention, shown are an ultrasonic aerosol drug delivery device with an alternative power supply 23.

It will be further apparent to one skilled in this art that the improvements provided for in the present invention, while described with relation to certain specific physical embodiments also lend themselves to being applied in another physical arrangements not specifically provided for herein, which are nonetheless within the spirit and scope of the invention taught here.

What is claimed is:

1. A device for ultrasonic drug delivery comprising:
   (a) means for producing oscillating non-radial ultrasonic waves, said means having a radiation surface; and
   (b) means for dispensing a liquid or powder drug onto the radiation surface to produce an aerosol spray upon contact of the dispensed liquid or powder drug with the radiation surface, said aerosol spray having drug particles energized by said oscillating ultrasonic waves;
   wherein the means for producing ultrasonic waves operates at a frequency in the range of 20 kHz to 200 kHz, such that said ultrasonic waves carry and direct said energized drug particles into a patient's mouth or onto another target for causing penetration of said drug particles below the tissue surface.

2. The device according to claim 1, wherein the means for producing the said oscillating ultrasonic waves comprises a piezofilm or disk, or a transducer tip.

3. The device according to claim 1, wherein the means for producing ultrasonic waves operates at about 100 MHz.

4. The device according to claim 1, wherein the radiation surface is arranged within the device such that the radiation surface is maintained at a distance from the patient's mouth or the target to be treated.

5. The device according to claim 1, wherein the radiation surface is positioned within the device at an angle with relation to the horizontal.

6. The device according to claim 5, wherein the radiation surface is positioned within the device at an angle with respect to the horizontal of from 0° to 90°.

7. The device according to claim 1, wherein the radiation surface is flat.

8. The device according to claim 1, wherein liquid droplets contact the radiation surface at one point and are atomized.

9. The device according to claim 1, wherein liquid droplets spread on the radiation surface and are atomized.

10. The device according to claim 1, wherein the means for producing ultrasonic waves operates at a fixed frequency.

11. The device according to claim 1, wherein the means for producing ultrasonic waves operates at a modulated frequency.

12. The device according to claim 1, wherein the means for producing ultrasonic waves operates at a pulsed frequency.

13. The device according to claim 1, wherein the means for producing ultrasonic waves produces waves which are sinusoidal.

14. The device according to claim 1, wherein the means for producing ultrasonic waves produces waves which are rectangular.

15. The device according to claim 1, wherein the means for producing ultrasonic waves produces waves which are trapezoidal.

16. The device according to claim 1, wherein the means for producing ultrasonic waves produces waves which are triangular.

17. The device according to claim 1, wherein the liquid or powder drug directed to the patient is precisely dosed with precision suitable for insulin dosing.

18. A method for ultrasonic drug delivery comprising:
   (a) providing a means for producing oscillating non-radial ultrasonic waves, said means having a radiation surface;
   (b) providing a means for dispensing a liquid or powder drug onto the radiation surface in order to produce an aerosol spray upon contact of the dispensed liquid or powder drug with the radiation surface, said aerosol spray having drug particles energized by said oscillating ultrasonic waves; and
   (c) propagating said drug particles into a patient's mouth or onto another target, said oscillating ultrasonic waves carrying and directing said energized drug particles for causing penetration of said drug particles below the tissue surface;
   wherein the means for producing ultrasonic waves operates at a frequency in the range of 20 kHz to 200 kHz.

19. A device for ultrasonic drug delivery comprising:
   (a) a transducer for producing ultrasonic waves, said transducer having a radiation surface positioned at a predetermined intersecting angle with respect to the horizontal; and
   (b) a dispenser for dispensing a fluid drug onto the radiation surface to produce an aerosol spray of drug particles having substantially uniform size, wherein the distance between the radiation surface and a dispensing end of the dispenser is greater than the diameter of a drop of fluid dispensed by the dispenser;

wherein the transducer operates at a frequency in the range of 20 kHz to 200 kHz, such that said ultrasonic waves carry and direct said energized drug particles into a patient's mouth or onto another target for causing penetration of said drug particles below the tissue surface.

20. The device according to claim 19, wherein the fluid drug is selected from the group consisting of antibiotics, antiseptics, saline, water, and oils.

21. The device according to claim 19, wherein the distance between the radiation surface and the dispensing end of the dispenser is greater than or equal to 0.5 mm.

22. A device for ultrasonic drug delivery comprising:
(a) a transducer for producing non-radial ultrasonic waves, said transducer having a radiation surface positioned at a predetermined intersecting angle with respect to the horizontal; and
(b) a dispenser for dispensing a powder drug onto the radiation surface to produce an aerosol spray of drug particles having substantially uniform size;
wherein the transducer operates at a frequency in the range of 20 kHz to 200 kHz, such that said ultrasonic waves carry and direct said energized drug particles into a patient's mouth or onto another target for causing penetration of said drug particles below the tissue surface.

23. A method for ultrasonic drug delivery comprising:
(a) providing a transducer for producing oscillating ultrasonic waves, said transducer having a radiation surface positioned at a predetermined intersecting angle with respect to the horizontal;
(b) providing a dispenser for dispensing a fluid drug onto the radiation surface in order to produce an aerosol spray of drug particles having substantially uniform size, wherein the distance between the radiation surface and a dispensing end of the dispenser is greater than the diameter of a drop of fluid dispensed by the dispenser;
(c) directing said substantially uniform size drug particles into contact with a patient; and
(d) operating said transducer at a frequency in the range of 20 kHz to 200 kHz, such that said ultrasonic waves carry and direct said energized drug particles into a patient's mouth or onto another target for causing penetration of said drug particles below the tissue surface.

24. The method according to claim 23, wherein the fluid drug is selected from the group consisting of antibiotics, antiseptics, saline, water, and oils.

25. The method according to claim 23, wherein the distance between the radiation surface and the dispensing end of the dispenser is greater than or equal to 0.5 mm.

26. A method for ultrasonic drug delivery comprising:
(a) providing a transducer for producing non-radial ultrasonic waves, said transducer having a radiation surface positioned at a predetermined intersecting angle with respect to the horizontal;
(b) providing a dispenser for dispensing a powder drug onto the radiation surface to produce an aerosol spray of drug particles having substantially uniform size;
(c) directing said substantially uniform size drug particles into contact with a patient; and
(d) operating said transducer at a frequency in the range of 20 kHz to 200 kHz, such that said ultrasonic waves carry and direct said energized drug particles into a patient's mouth or onto another target for causing penetration of said drug particles below the tissue surface.

* * * * *